United States Patent
Kim et al.

(10) Patent No.: US 12,303,588 B2
(45) Date of Patent: May 20, 2025

(54) **COMPOSITION CONTAINING *Cirsium japonicum* EXTRACT AS ACTIVE INGREDIENT FOR STIMULATING MELANOGENESIS**

(71) Applicant: BIOSPECTRUM, INC., Yongin-si (KR)

(72) Inventors: Min Kyung Kim, Seongnam-si (KR); Da Hee Son, Yongin-si (KR); Seoung Woo Shin, Seongnam-si (KR); Eun Sun Jung, Suwon-si (KR); Deok Hoon Park, Seongnam-si (KR)

(73) Assignee: BIOSPECTRUM, INC., Yongin-si (KR)

( * ) Notice: Subject to any disclaimer, the term of this patent is extended or adjusted under 35 U.S.C. 154(b) by 441 days.

(21) Appl. No.: 17/831,558

(22) Filed: Jun. 3, 2022

(65) Prior Publication Data
US 2022/0287956 A1    Sep. 15, 2022

Related U.S. Application Data

(62) Division of application No. 16/496,565, filed as application No. PCT/KR2018/002898 on Mar. 12, 2018, now abandoned.

(30) Foreign Application Priority Data

Mar. 21, 2017    (KR) .................. 10-2017-0035571

(51) Int. Cl.
*A61K 8/9789*    (2017.01)
*A61K 36/28*    (2006.01)
*A61Q 5/10*    (2006.01)
*A61Q 19/04*    (2006.01)

(52) U.S. Cl.
CPC ............ *A61K 8/9789* (2017.08); *A61K 36/28* (2013.01); *A61Q 5/10* (2013.01); *A61Q 19/04* (2013.01); *A61K 2800/78* (2013.01)

(58) Field of Classification Search
None
See application file for complete search history.

(56) References Cited

U.S. PATENT DOCUMENTS 10,537,516 B2 *    1/2020    Zhang .................. A61K 8/9794

FOREIGN PATENT DOCUMENTS

| | | |
|---|---|---|
| FR | 2834718 | 7/2003 |
| JP | 2001131026 | 5/2001 |
| JP | 2001131032 | 5/2001 |
| JP | 2003-171240 | 6/2003 |
| JP | 2013-059592 | 8/2013 |
| JP | 2013159592 | 8/2013 |
| KR | 10-2007-0021522 | 2/2007 |
| KR | 2017-0025375 | 3/2017 |
| KR | 101989407 | 6/2019 |
| TW | I257309 | 7/2006 |
| WO | 2001-034102 | 5/2001 |
| WO | 2003-059368 | 7/2003 |

OTHER PUBLICATIONS

Yeo (KR 20170025375—English translation)—Mar. 8, 2017.*
Kang (KR 2015049366—English translation) 2015.*
Chinese Herbal Medicine Database (https://herbaltcm.sn.polyu.edu.hk/herbal/japanese-thistle-herb)—accessed Jan. 2025.*

* cited by examiner

*Primary Examiner* — Susan Hoffman
(74) *Attorney, Agent, or Firm* — LEX IP MEISTER, PLLC

(57) ABSTRACT

The present invention relates to a composition for stimulating melanogenesis, comprising *Cirsium japonicum* extract as an effective ingredient. The composition has no skin irritation and cytotoxicity and is excellent in human stability and very effective in stimulating melanogenesis. Therefore, the composition can be safely used in cosmetic or pharmaceutical composition for preventing, improving or treating vitiligo, white hair or hypopigmentation.

6 Claims, 2 Drawing Sheets

[FIG. 1]
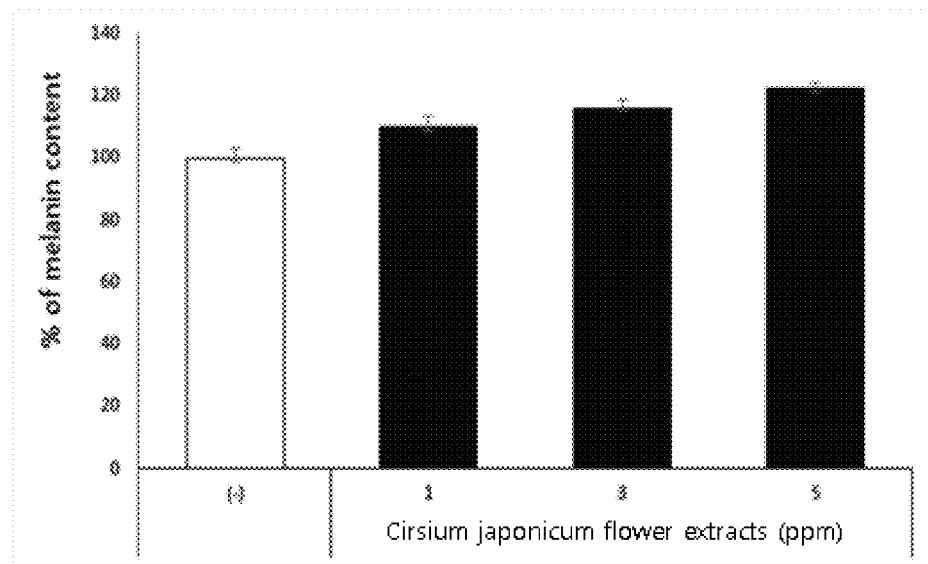
[FIG. 2]
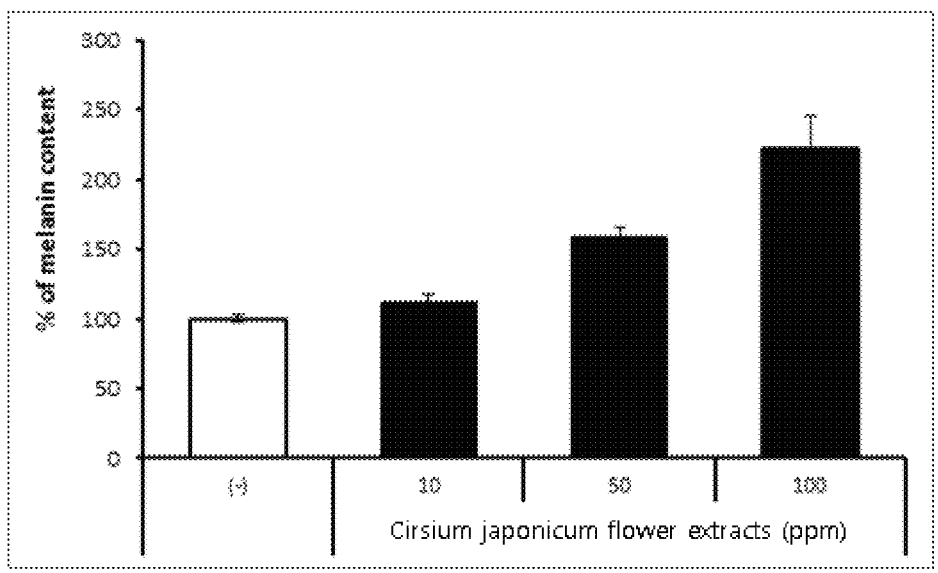

[FIG. 3]
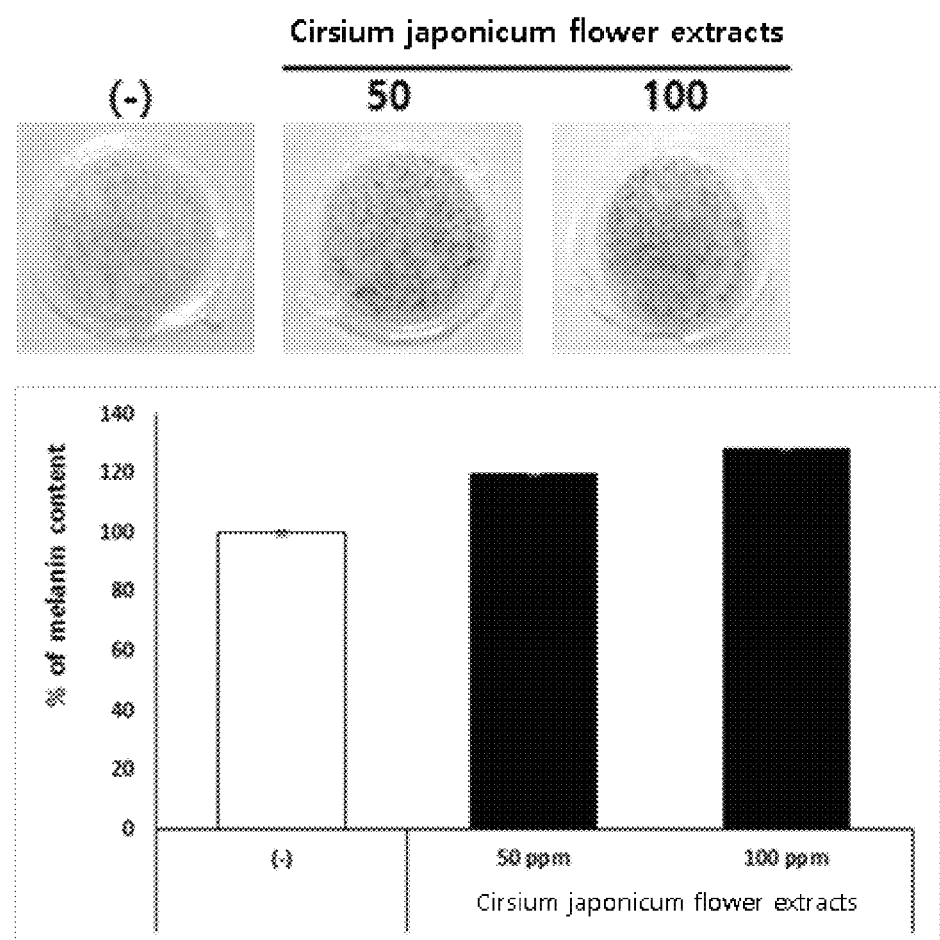

COMPOSITION CONTAINING *Cirsium japonicum* EXTRACT AS ACTIVE INGREDIENT FOR STIMULATING MELANOGENESIS

TECHNICAL FIELD

The present invention relates to a composition for stimulating melanogenesis comprising *Cirsium japonicum* extracts as active ingredient, more particularly, which promote melanin production, induce blackening, and can treat, improve, or prevent vitiligo, gray hair, or hypochromatism.

BACKGROUND ART

Melanin produced in melanin cell (melanocyte) existing in the epidermal basal layer of human skin refers to a phenolic polymer having complex form of black pigment and protein. Such melanin determines human skin color by its concentration and distribution and plays the role of protecting human skin from UV rays.

If melanin is excessively produced, it causes pigmentation such as freckle, ephelis, etc. On the contrary, if melanin production is excessively suppressed, it may lead to skin disease of vitiligo, gray hair by a decrease of number and function in melanocyte, or hypochromatin which can be risk factor for skin cancer. Therefore, as much as whitening related study of suppressing melanin production, study of inducing blackening by stimulating melanogenesis is also very important.

These vitiligo, gray hair and hypochromatism do not only look good outside but also cause many difficulties in social activities. Thus, for vitiligo and hypochromatism, there are many cases of treatment using surgical procedure or temporarily hiding with external skin applications such as cosmetics, and for gray hair, many people try to temporarily hide the gray hair with dyeing. However, since such methods are not their fundamental methods of prevention, improvement or treatment, it is necessary to study melanin production accelerator for more fundamental solution.

With this regard, Korean Patent Registration No. 10-1669359 disclose a composition for stimulating melanin synthesis containing mixture of *Rhododendron schlippenbachii* extract, *Lespedeza bicolor* extract and *Quercus variabilis* extract, but the above composition has the problem of complex raw material preparation and manufacturing process since it mixes and uses several extracts.

On the other hand, *Cirsium japonicum* is perennial belonging to compositae which is widely used for private and Korean medicine prescription, and young sprouts are used for food. Generic name of *Cirsium japonicum, Cirsium*, is from Greek word meaning vein cure, and it originated from the use as drug curing disease of vein inflating from ancient times. *Cirsium japonicum* contains various secondary metabolites with excellent physiological activity such as apigenin, myricetin, luteolin and kaempferol, and it is known to have effect for hydrolymph, hemostasis, extravasated blood removal, boil cure, etc.

With regard to the efficacy of the above *Cirsium japonicum*, Korean Patent Registration No. 10-1281710 discloses obesity treatment and prevention effect of *Cirsium japonicum* extract, and Korean Patent Publication No. 10-2017-0025375 discloses skin regeneration, skin wrinkle improvement, skin whitening effect, etc. of *Cirsium japonicum* extract, but it is not yet disclosing the melanin synthesis acceleration effect of *Cirsium japonicum* extract.

Accordingly, the present inventors have made extensive efforts to develop natural material, which is harmless to the human body and has excellent effect to stimulate melanocytes, to fundamentally solve vitiligo, gray hair and hypochromatin, As a result, the present inventors have found that a composition comprising *Cirsium japonicum* extract induces blackening by stimulating melanocytes and is excellent in the human body stability without skin irritation and cell toxicity, and then have completed the present invention.

DISCLOSURE

Technical Problem

It is an object of the present invention to provide a composition for stimulating melanogenesis.

It is another object of the present invention to provide a cosmetic composition for preventing or improving vitiligo, gray hair or hypochromatism comprising the above melanogenesis stimulating composition.

It is still another object of the present invention to provide a pharmaceutical composition for preventing or treating vitiligo, gray hair or hypochromatism comprising the above melanogenesis stimulating composition.

It is still another object of the present invention to provide a food composition for preventing or improving vitiligo, gray hair or hypochromatism comprising the above melanogenesis stimulating composition.

Technical Solution

In order to achieve the above objectives, the present invention provides composition for stimulating melanogenesis comprising *Cirsium japonicum* extract as an active ingredient.

In order to achieve another above objective, the present invention provides a cosmetic composition for preventing or improving vitiligo, gray hair or hypochromatism, comprising *Cirsium japonicum* extract as active ingredient.

In order to achieve still another above objective, the present invention provides a pharmaceutical composition, for preventing or treating vitiligo, gray hair or hypochromatism comprising *Cirsium japonicum* extract as active ingredient.

In order to achieve still another above objective, the present invention provides a food composition for preventing or improving vitiligo, gray hair or hypochromatism, comprising *Cirsium japonicum* extract as active ingredient.

In order to achieve still another above objective, the present invention provides a method of preventing, improving or treating vitiligo, gray hair or hypochromatism of a subject by administering said composition comprising *Cirsium japonicum* extract as active ingredient to the subject and by stimulating melanogenesis of the subject.

In the present invention, *Cirsium japonicum* is perennial belonging to compositae which is widely used for private and Korean medicine prescription, and its young sprout are used for food.

In the present invention, *Cirsium japonicum* extract means that is extracted from any one or more selected from the group consisting of flowers, leaves, stems, roots and whole plant of *Cirsium japonicum*, and preferably means that is extracted from flowers of *Cirsium japonicum*.

The *Cirsium japonicum* extract according to the present invention promotes the production of melanocyte, which is a pigment cell, and increases the synthesis of melanin by activating the produced melanocytes, resulting in repigmentation.

The *Cirsium japonicum* extract of the present invention can be extracted solvent known in the art and the extracted liquid can be used in liquid form or concentrated and/or dried form. Herein, the solvent may be an extraction solvent selected from water, an anhydrous or hydrated lower alcohol having 1 to 4 carbon atoms (methanol, ethanol, propanol, butanol and the like), a mixed solvent of the lower alcohol with water, acetone, ethyl acetate, chloroform or 1,3-butylene glycol. Preferably, the solvent may be an extraction solvent selected from methanol, ethanol, or butanol. However, the present invention is not limited thereto, and since the extraction degree and loss degree of the active ingredient of the extract may vary depending on the organic solvent to be extracted, it is preferable to select and use an appropriate organic solvent.

Examples of the extraction method include, but are not limited to, cooling immersion extraction method, ultrasonic extraction method, or reflux cooling extraction method, and the like. It is preferable to carry out by the ultrasonic extraction method.

Above ultrasonic extraction is a method of extracting useful components from various natural materials at room temperature with physical force, not chemical force, using vibrating element with 20,000 or more vibrations per second. Unlike solvent extraction, vegetable oil extraction or water steam distillation extraction, ultrasonic extraction has the advantage of being able to extract at a high concentration without destroying the active components contained in the natural material at room temperature.

As one specific example, the ultrasonic extraction may be performed for 24 to 72 hours at room temperature for the dried *Cirsium japonicum* powder in 60 to 80% ethanol solution. Preferably, it is carried out for 36 to 60 hours at room temperature in 65% to 75% ethanol solution. More preferably, it is carried out for 48 hours at room temperature in 70% ethanol solution. If the value is below the above lower limit, the active components contained in *Cirsium japonicum* is not sufficiently extracted. If the upper limit is exceeded, there is no significant difference in the extraction amount of the active components, and impurities other than the active components are extracted and the efficiency of the process is reduced.

The unripe *Cirsium japonicum* extract of the present invention comprises all extracts, fractions and refinings obtained from the respective steps of extraction, fractionation or purification.

The *Cirsium japonicum* extract of the present invention is comprised in the composition of the present invention in an amount of 0.0001 to 70.0% by weight, preferably 0.001 to 68.0% by weight relative to the weight of total composition. When the weight of the *Cirsium japonicum* extract is less than 0.0001% by weight, it cannot be expected to promote the melanin production, and when it is greater than 70% by weight, an increase of the effect according to the increase of the content of the *Cirsium japonicum* extract is very weak and there is a problem in preparing a pharmaceutical formulation.

In one specific aspect, the composition for stimulating melanogenesis comprising the *Cirsium japonicum* extract of the present invention as an active ingredient may be used a cosmetic composition or a pharmaceutical composition for the prevention, improvement or treatment of vitiligo, white hair or hypopigmentation caused by the destruction or dysfunction of melanocytes.

The vitiligo is a phenomenon in which melanocytes are destroyed by abnormalities of autoimmune function and white spots of various sizes and shapes appear on the skin, and it refers to acquired depigmentation disease.

The gray hair refers to a phenomenon in which the hair turns white while the number and functionality of melanocytes in hair root decrease.

Hypochromatism refers to a disease in which local melanocytes are functional disorder due to skin diseases such as eczema, atopic dermatitis, and inflammatory dermatitis, and the skin at the lesion site becomes white temporarily.

In the present invention, the prevention, improvement or treatment of vitiligo, gray hair or hypochromatism stimulates inactive melanocytes or pigmented hair cells present in the skin or hair follicle to promote differentiation, proliferation and migration of these cells, and produce melanin. Thereby, the symptoms of vitiligo, gray hair or hypochromatism are prevented, improved or treated.

According to one embodiment of the present invention, the present invention provides a cosmetic composition that is effective in the prevention or improvement of vitiligo, white hair or hypopigmentation by promoting the production of melanin in the cell by including *Cirsium japonicum* extract as an active ingredient.

The *Cirsium japonicum* extract of the present invention is comprised in the cosmetic composition of the present invention in an amount of 0.0001 to 15.0% by weight, preferably 0.001 to 10.0% by weight relative to the weight of total composition. When the weight of the *Cirsium japonicum* extract is less than 0.0001% by weight, it cannot be expected to prevent or improve vitiligo, white hair or hypopigmentation, and when it is greater than 15% by weight, there is a problem in preparing a cosmetic formulation.

The cosmetic composition of the present invention may further contain, in addition to *Cirsium japonicum* extract as an effective ingredient, components that are conventionally used in cosmetic compositions. Examples of the components include conventional auxiliaries, such as antioxidants, stabilizers, solubilizers, vitamins, pigments and fragrances, and carriers.

The cosmetic composition may be prepared in any formulation commonly prepared in the art. For example, it may be formulated as a solution, a suspension, an emulsion, a paste, a gel, a cream, a lotion, a powder, a soap, a surfactant-containing cleanser, an oil, a powdered foundation, an emulsion foundation, a wax foundation, a spray, or the like. More specifically, the cosmetic composition may be formulated into a nutrient cream, a lotion astringent, a softening toner, a lotion, an essence, a nutrient gel, or massage cream, or the like. But it is not particularly limited there to.

When the formulation of the cosmetic composition is the paste, cream or gel, animal oil, vegetable oil, wax, paraffin, starch, tragacanth gum, cellulose derivative, polyethylene glycol, silicone, bentonite, silica, talc or zinc oxide, etc. can be used as the carrier ingredient.

When the formulation of the cosmetic composition is the powder or spray, the lactose, talc, silica, aluminum hydroxide, calcium silicate or polyamide powder can be utilized, and in particular when it is the spray, a propellant such as chlorofluorohydrocarbon, propane/butane or dimethyl ether can be additionally included.

When the formulation of the cosmetic composition is the solution or turbid fluid, the solvent, solubilizing agent or emulsifying agent can be utilized as a carrier ingredient. For example, water, ethanol, isopropanol, ethyl carbonate, ethyl acetate, benzyl alcohol, benzyl benzoate, propylene glycol, 1,3-buthylglycol oil, glycerol aliphatic ester, polyethylene glycol or aliphatic ester of sorbitan, etc. can be utilized as the carrier ingredient.

When the formulation of the cosmetic composition is suspension, the liquid diluents such as water, ethanol or propylene glycol, suspending agent such as ethoxylated isostearyl alcohol, polyoxyethylene sorbitol ester and polyoxyethylene sorbitan ester, microcrystalline cellulose, aluminum metahydroxide, bentonite, agar, or tragacant, etc. can be utilized as the carrier ingredient.

When the formulation of the cosmetic composition is the surfactant-containing cleansing, the aliphatic alcohol sulfate, aliphatic alcohol ether sulfate, sulphosuccinic monoester, isethionate, imidazolinium derivative, methyltaurate, sarcosinate, fatty acid amide ether sulfate, alkylamidobetaine, aliphatic alcohol, fatty acid glyceride, fatty acid diethanolamide, vegetable oil, lanoline derivative or ethoxylated glycerol fatty acid ester, etc. can be utilized as the carrier ingredient.

According to one embodiment of the present invention, the present invention provides a pharmaceutical composition that is effective in the prevention or treatment of vitiligo, white hair or hypopigmentation by promoting the production of melanin in the cell by including *Cirsium japonicum* extract as an active ingredient.

The *Cirsium japonicum* extract of the present invention is comprised in the pharmaceutical composition of the present invention in an amount of 0.0001 to 70.0% by weight, preferably 0.001 to 68.0% by weight relative to the weight of total composition. When the weight of the *Cirsium japonicum* extract is less than 0.0001% by weight, it cannot be expected to prevent or treat vitiligo, white hair or hypopigmentation, and when it is greater than 70.0% by weight, there is a problem in preparing a pharmaceutical formulation.

The pharmaceutical composition may further contain, in addition to *Cirsium japonicum* extract as an effective ingredient, a carrier that is conventionally acceptable in the pharmaceutical composition.

The carrier suitable for the pharmaceutical composition is the carrier commonly used in the formulation. The carrier includes, but not limited to, carbohydrate compounds (e.g. lactose, amylose, dextrose, sucrose, sorbitol, mannitol, starch, cellulose etc.), acacia gum, calcium phosphate, alginate, gelatin, calcium silicate, microcrystalline cellulose, polyvinylpyrrolidone, celloluse, water, syrup, salt solution, alcohol, gum Arabic, vegetable oils (e.g. corn oil, cotton seed oil, soy milk, olive oil. Coconut oil), polyethylene glycol, methyl cellulose, methylhydroxy benzoate, prophylhydroxy benzoate, talc, magnesium stearate, mineral oil, and the like.

In addition to the above components, the pharmaceutical composition of the present invention may further include a lubricant, a humectant, a sweetener, a flavoring agent, an emulsifier, a suspending agent, a preservative, and the like. The suitable pharmaceutically acceptable carrier or agents are specifically disclosed in, for example, Remington's Pharmaceutical Sciences (19$^{th}$ ed., 1995).

The pharmaceutical composition of the present invention can be administered orally or parenterally to mammals such as rats, mice, livestock, humans, etc. and can be applied, preferably, by parenteral administration, more preferably in the manner of topical application by application.

The effective dose level of the pharmaceutical composition can be variously determined by the method of formulation, mode of administration, age, weight, health and sex of a patient, food, time of administration, route of administration, rate of excretion and sensitivity of the patient to the drug and the like. Oral dosages of the pharmaceutical compositions of the present invention are in the range of 0.001-300 mg/kg (body weight) on an adult basis. In addition, in the case of external preparations, it is preferable to apply once to 5 times a day in an amount of 1.0 to 3.0 ml on an adult basis and continue for 1 month or more. However, the dosage does not limit the scope of the present invention.

The cosmetic or pharmaceutical composition comprising the *Cirsium japonicum* extract of the present invention as an active ingredient stimulating melanogenesis of the subject by administration, such as administration in the subject, subcutaneous administration or topical application by application to a subject, and melanin synthesis is increased by activation of the resulting melanocytes and then the pigment re-deposition (repigmentation) is occurred. Therefore, the cosmetic or pharmaceutical composition has an advantage that can achieve the purpose of alleviating, getting better, preventing, improving or treating vitiligo, white hair or hypopigmentation.

In one specific embodiment, the present invention provides a method and use thereof for improving vitiligo, white hair and hypopigmentation of a subject by administering to the subject a composition for stimulating melanogenesis comprising *Cirsium japonicum* extract as an active ingredient.

The composition administered to the subject has an effect of improving or treating vitiligo, white hair and hypopigmentation of the subject due to the melanin production promoting effect as described above.

The term, "subject" in the present invention means a mammal such as monkey, cow, horse, pig, sheep, dog, cat, rat, mouse, chimpanzee, etc., including human, having the disease symptom of which can be alleviated by administering the composition of the present invention.

In the present invention, the term "improvement" means (a) inhibition of a development, (b) alleviation and (c) removal of the vitiligo, white hair and hypopigmentation resulting from disruption or dysfunction of melanocytes in a subject.

On the other hand, *Cirsium japonicum* extract of the present invention is a natural extract that has no skin irritation and cytotoxicity and excellent human stability and has almost no side effects on the human body, and thus is very effective in stimulating melanogenesis. It can be safely used as an active ingredient in therapeutic cosmetics or pharmaceutical compositions.

In another specific embodiment, the present invention provides a method for preventing, improving, or treating vitiligo, white hair or hypopigmentation by promoting the production of melanin by administering to a subject a composition comprising the *Cirsium japonicum* extract as an active ingredient.

The subject is a mammal, including humans, which is intended to improve vitiligo, white hair or hypopigmentation by stimulating melanogenesis.

The administration is oral or parenteral administration, preferably parenteral administration, more preferably topical administration by application. The dosage and the like can be easily changed and used by those skilled in the art the method of formulation, mode of administration, age, weight, sex of a patient, morbidity, etc.

By administering to the subject a composition for the prevention, improvement or treatment of vitiligo, white hair or hypopigmentation according to the present invention, the melanin production of the subject may be promoted to prevent and improve vitiligo, white hair or hypopigmentation.

Advantageous Effects

The composition for stimulating melanogenesis comprising *Cirsium japonicum* extract as an effective ingredient has no skin irritation and cytotoxicity and is excellent in human stability and very effective in stimulating melanogenesis. Therefore, the composition can be safely used in cosmetic or pharmaceutical composition for preventing, improving or treating vitiligo, white hair or hypopigmentation.

DESCRIPTION OF DRAWINGS

FIG. 1 shows the melanin synthesis promoting effect depending on the concentration of *Cirsium japonicum* extract in human melanocyte.

FIG. 2 shows the melanin synthesis promoting effect depending on the concentration of *Cirsium japonicum* extract in B16 melanoma cell.

FIG. 3 shows the melanin synthesis promoting effect depending on the concentration of *Cirsium japonicum* extract in 3D skin.

BEST MODE FOR INVENTION

In order to achieve the above object, the present invention provides a composition for stimulating melanogenesis comprising *Cirsium japonicum* extract as an active ingredient.

In order to achieve the above another object, the present invention provides a cosmetic composition for preventing or improving vitiligo, white hair or hypopigmentation, characterized in that it comprises *Cirsium japonicum* extract as an active ingredient.

In order to achieve the above another object, the present invention provides a pharmaceutical composition for preventing or treating vitiligo, white hair or hypopigmentation, characterized in that it comprises *Cirsium japonicum* extract as an active ingredient.

In order to achieve the above another object, the present invention provides a method for preventing, improving or treating vitiligo, white hair or hypopigmentation by promoting the melanin production by administering to the subject a composition comprising the *Cirsium japonicum* extract as an active ingredient.

Hereinafter, the present invention will be given in detail through Examples. The Examples is given only to more specifically describe the present invention, and it will be self-evident to the ordinary person in the art to which the present invention subject that the scope of the present invention is not limited to such Examples.

Example 1: The Preparation of *Cirsium japonicum* Extract

*Cirsium japonicum* flowers were harvested and washed thoroughly to remove any foreign matter and impurities. It was dried at 20 to 35° C. and then ground to a particle size of 1 mm or less. Thereafter, 1 kg of the *Cirsium japonicum* flower powder was soaked in 70% ethanol solvent, sonicated for 48 hours, and the obtained extract was filtered using filter paper (Advantes, No. 2). The filtrate was concentrated under reduced pressure to prepare *Cirsium japonicum* extract.

Example 2: Measurement of the Melanin Promoting Effect of *Cirsium japonicum* Extract in Human Melanocytes Human melanocytes were inoculated into 6-well plate containing M254 medium with HMGS (Human Melanocytes Growth Supplement) at a density $1.5 \times 10^5$ cells per well, and then cultured in 5% concentration of $CO_2$ cultivator under the condition of 37° C. until at least about 80% adhered to the bottom of the well. Thereafter, the medium was removed and the sample of Example 1 was replaced with a medium diluted to an appropriate concentration, and then incubated in 5% concentration of $CO_2$ under the condition of 37° C. for 5 days. The concentration range of *Cirsium japonicum* extract according to Example 1 was determined to be 1 ppm, 3 ppm, 5 ppm without cytotoxicity. The cells from which the medium was removed were washed with PBS (phosphated buffersaline), and the cells were obtained. The obtained cells were counted using a hemocytometer and then centrifuged at 10,000 to 13,000 rpm for 10 minutes to remove the supernatant and pellets were obtained. The obtained cell pellet was dried at 60° C., and then 100 µl of 1M sodium hydroxide solution containing 10% DMSO was added to obtain an intracellular melanin solution in a 60° C. thermostat. Using this solution, the absorbance at 450 nm was measured with a microplate reader to determine the amount of melanin per cell. The results are shown in Table 1 and FIG. 1.

TABLE 1

| Sample | Treatment concentration (ppm) | Melanin production promotion ratio (%) |
| --- | --- | --- |
| Control | — | 100 |
| *Cirsium japonicum* extract | 1 | 110 |
|  | 3 | 116 |
|  | 5 | 122 |

As shown in Table 1 and FIG. 1, *Cirsium japonicum* extract according to the present invention was observed to increase the rate of melanin production in a concentration-dependent compared to the control. Therefore, *Cirsium japonicum* extract according to the present invention was found to have the effect of promoting the production of melanin.

Example 3: Measurement of the Melanin Promoting Effect of *Cirsium japonicum* Extract in B16 Melanoma Cells B16 melanoma cells were inoculated into 6-well plate containing DMEM medium with 10% FBS (Fetal Bovine Serum) at a density $1.5 \times 10^5$ cells per well, and then cultured in 5% concentration of $CO_2$ cultivator under the condition of 37° C. until at least about 80% adhered to the bottom of the well. Thereafter, the medium was removed and the sample of Example 1 was replaced with a medium diluted to an appropriate concentration, and then incubated in 5% concentration of $CO_2$ under the condition of 37° C. for 3 days.

The concentration range of *Cirsium japonicum* extract according to Example 1 was determined to be 10 ppm, 50 ppm, 100 ppm without cytotoxicity. The cells from which the medium was removed were washed with PBS (phosphated buffersaline), and the cells were obtained. The obtained cells were counted using a hemocytometer and then centrifuged at 10,000 to 13,000 rpm for 10 minutes to remove the supernatant and pellets were obtained. The obtained cell pellet was dried at 60° C., and then 100 μl of 1M sodium hydroxide solution containing 10% DMSO was added to obtain an intracellular melanin solution in a 60° C. thermostat. Using this solution, the absorbance at 450 nm was measured with a microplate reader to determine the amount of melanin per cell. The results are shown in Table 2 and FIG. 2.

TABLE 2

| Sample | Treatment concentration (ppm) | Melanin production promotion ratio (%) |
|---|---|---|
| Control | — | 100 |
| *Cirsium japonicum* extract | 10 | 111 |
|  | 50 | 159 |
|  | 100 | 222 |

As shown in Table 2 and FIG. 2, *Cirsium japonicum* extract according to the present invention was observed to increase the rate of melanin production in a concentration-dependent compared to the control. When *Cirsium japonicum* extract was treated with 100 ppm, it was observed that the melanin production was promoted more than two times compared to the control. Therefore, *Cirsium japonicum* extract according to the present invention was found to have the effect of promoting the production of melanin.

Example 4: Measurement of the Melanin Promoting Effect of *Cirsium japonicum* Extract in 3D Skin 3D skin were inoculated into 6-well plate containing maintenance medium, and then cultured in 5% concentration of $CO_2$ cultivator under the condition of 37° C. Thereafter, the medium was removed, and the *Cirsium japonicum* extracts were treated at ppm and 100 ppm without cytotoxicity. *Cirsium japonicum* extract was replaced three times with a concentration-treated medium for 10 days and then incubated at 5% $CO_2$ and 37° C. The cells from which the medium was removed were washed with PBS (phosphated buffersaline), and the cells were obtained. The obtained cells were centrifuged at 10,000 to 13,000 rpm for 10 minutes to remove the supernatant and pellets were obtained. The obtained cell pellet was dried at 60° C., and then 100 μl of 1M sodium hydroxide solution containing 10% DMSO was added to obtain an intracellular melanin solution in a 60° C. thermostat. Using this solution, the absorbance at 450 nm was measured with a microplate reader to determine the amount of melanin per cell. The results are shown in Table 3 and FIG. 3.

TABLE 3

| Sample | Treatment concentration (ppm) | Melanin production promotion ratio (%) |
|---|---|---|
| Control | — | 100 |
| *Cirsium japonicum* extract | 50 | 120 |
|  | 100 | 128 |

As shown in Table 3 and FIG. 3, *Cirsium japonicum* extract according to the present invention was observed to increase the rate of melanin production in a concentration-dependent compared to the control. Therefore, *Cirsium japonicum* extract according to the present invention was found to have the effect of promoting the production of melanin.

Example 5: Test for Identifying the Safety of *Cirsium japonicum* Extract to the Human Skin In order to identify as to whether the *Cirsium japonicum* extract is safe or not, a test for identifying the safety to the human skin was performed. For this, a cumulative skin irritation was carried out.

A nutritious cream containing 0.1%, 0.5% and 1% of *Cirsium japonicum* extracts of Example 1, respectively, was prepared. Specifically, purified water, triethanolamine, and propylene glycol were heated and dissolved at a temperature of 70° C. (aqueous phase). Beeswax, liquid paraffin, oily ingredients, emulsifiers and preservatives were heated and dissolved at a temperature of 70° C. (oil phase). The oil phase was added to the aqueous phase to prepare an emulsion. After emulsification was completed, the solution was cooled to 45° C., and *Cirsium japonicum* extracts were added 0.1%, 0.5% and 1% respectively, dispersed and then cooled to 30° C. As the content of the *Cirsium japonicum* extract was increased to 0.1%, 0.5% and 1%, the nutritional cream was prepared by reducing the content of the liquid paraffin to 9.91%, 9.51% and 9.01%, respectively.

The nourishing cream prepared as described above was applied as a patch to areas of humerus of 30 adults for accumulated 24 hours on alternate day in total 9 times to test as to whether the *Cirsium japonicum* extract stimulates the skin.

The patch used Finn chamber (Epitest Ltd, Filand) and the patch was practiced after dropping with 15111 of the skin external preparations prepared from the above, respectively. The degree of the reaction represented on the skin in every time was scored by using the below experimental formula 1. The results are represented in Table 4.

Mean reaction degree=[{(reaction index×reaction degree)/(total number of the subject×the highest score (four point))}×100]/times of the test (9times)  [Experimental Formula 1]

In regard to the response degree, 1 point was provided for ±, 2 points for +, and 4 points for ++. When the mean reaction degree is less than 3, it is considered as being the safe composition.

TABLE 4

| Test material | Number of subjects showing response | | | | | | | | | Average response degree |
|---|---|---|---|---|---|---|---|---|---|---|
| | 1st week | | | 2nd week | | | 3rd week | | | |
| | 1st ± + ++ | 2nd ± + ++ | 3rd ± + ++ | 4th ± + ++ | 5th ± + ++ | 6th ± + ++ | 7th ± + ++ | 8th ± + ++ | 9th ± + ++ | |
| Control group (Squalene) | 1 - - | 0 - - | - - - | - - - | - - - | - - - | - - - | - - - | - - - | 0.09 |
| Cirsium japonicum extract (0.1%) [Test group 1] | 0 - - | 0 - - | - - - | - - - | - - - | - - - | - - - | - - - | - - - | 0.00 |
| Cirsium japonicum extract (0.5%) [Test group 2] | 0 - - | 0 - - | - - - | - - - | - - - | - - - | - - - | - - - | - - - | 0.00 |
| Cirsium japonicum extract (1%) [Test group 3] | 0 - - | 0 - - | - - - | - - - | - - - | - - - | - - - | - - - | - - - | 0.00 |

As shown in the above Table 4, in all of the test groups 1, 2, and 3, all numbers of subjects belonging to ±, +, ++ were 0 and Average response degree was also 0.00. As a result of the above test, test group are all less than 3, and thus, it was determined that the *Cirsium japonicum* extract is safe for use on human skin which does not show clear cumulative skin irritation.

The composition of the present invention may be prepared as an example as follows but is not limited thereto.

Preparation Example 1: Preparation of Cosmetics 1-1. Preparation of Softening Toner Shown in Table 5 below, a softening toner containing the *Cirsium japonicum* extract as an active ingredient was prepared according to a conventional method.

TABLE 5

| Component | Content (wt %) |
|---|---|
| *Cirsium japonicum* extract | 0.01 |
| Glycerin | 3.0 |
| Butylene glycol | 2.0 |
| Propylene glycol | 2.0 |
| Carboxyvinyl polymer | 0.1 |
| Ethanol | 10.0 |
| Triethanolamine | 0.1 |
| Preservative, trace amount of pigment, trace amount of fragrance, and trace amount of purified water | 82.79 |
| Total | 100.0 |

1-2. Preparation of Nourishin Toner

Shown in Table 6 below, a nourishing toner containing the *Cirsium japonicum* extract as an active ingredient was prepared according to a conventional method.

TABLE 6

| Component | Content (wt %) |
|---|---|
| *Cirsium japonicum* extract | 0.01 |
| Beeswax | 4.0 |
| Polysorbate 60 | 1.5 |
| Sorbitan sesquioleate | 0.5 |
| Liquid paraffin | 5.0 |
| Squalane | 5.0 |
| caprylic/capric triglyceride | 5.0 |
| Glycerin | 3.0 |
| Butylene glycol | 3.0 |
| Propylene glycol | 3.0 |
| Carboxyvinyl polymer | 0.1 |
| Triethanolamine | 0.2 |
| Preservative, trace amount of pigment, trace amount of fragrance, and trace amount of purified water | 69.69 |
| Total | 100.0 |

1-3. Preparation of Nourishing Cream

Shown in Table 7 below, a nourishing cream containing the *Cirsium japonicum* extract as an active ingredient was prepared according to a conventional method.

TABLE 7

| Component | Content (wt %) |
|---|---|
| *Cirsium japonicum* extract | 0.01 |
| Beeswax | 10.0 |
| Polysorbate 60 | 1.5 |
| Sorbitan sesquioleate | 0.5 |
| Liquid paraffin | 10.0 |
| Squalane | 5.0 |
| caprylic/capric triglyceride | 5.0 |
| Glycerin | 5.0 |
| Butylene glycol | 3.0 |
| Propylene glycol | 3.0 |
| Triethanolamine | 0.2 |
| Preservative, trace amount of pigment, trace amount of fragrance, and trace amount of purified water | 56.79 |
| Total | 100.0 |

1-4. Preparation of Massage Cream

Shown in Table 8 below, a massage cream containing the *Cirsium japonicum* extract as an active ingredient was prepared according to a conventional method.

TABLE 8

| Component | Content (wt %) |
|---|---|
| *Cirsium japonicum* extract | 0.01 |
| Beeswax | 10.0 |
| Polysorbate 60 | 1.5 |
| Sorbitan sesquioleate | 0.8 |
| Liquid paraffin | 40.0 |
| Squalane | 5.0 |
| caprylic/capric triglyceride | 4.0 |
| Glycerin | 5.0 |
| Butylene glycol | 3.0 |
| Propylene glycol | 3.0 |
| Triethanolamine | 0.2 |
| Preservative, trace amount of pigment, trace amount of fragrance, and trace amount of purified water | 27.49 |
| Total | 100.0 |

1-5. Preparation of Pack

Shown in Table 9 below, a pack containing the *Cirsium japonicum* extract as an active ingredient was prepared according to a conventional method.

TABLE 9

| Component | Content (wt %) |
|---|---|
| *Cirsium japonicum* extract | 0.01 |
| Polyvinyl alcohol | 13.0 |
| Sodium carboxymethyl cellulose | 0.2 |
| Allantoin | 0.1 |
| Ethanol | 5.0 |
| Nonyl phenyl ether | 0.3 |
| Preservative, trace amount of pigment, trace amount of fragrance, and trace amount of purified water | Balance |
| Total | 100.0 |

Preparation Example 2: Preparation of Pharmaceutical Preparation 2-1. Preparation of Powder Formulation

TABLE 10

| Component | Content (g) |
|---|---|
| *Cirsium japonicum* extract | 2 |
| Lactose | 1 |

The above components were mixed with each other and then filled in a sealed bag, thereby preparing a powder formulation containing *Cirsium japonicum* extract as an active ingredient.

2-2: Preparation of Tablet Formulation

TABLE 11

| Component | Content (mg) |
|---|---|
| *Cirsium japonicum* extract | 100 |
| Corn starch | 100 |
| Lactose | 100 |
| Magnesium stearate | 2 |

The above components were mixed with each other and then compressed to a tablet according to a conventional method, thereby preparing a tablet formulation containing *Cirsium japonicum* extract as an active ingredient.

2-3. Preparation of Capsule Formulation

TABLE 12

| Component | Content (mg) |
|---|---|
| *Cirsium japonicum* extract | 100 |
| Corn starch | 100 |
| Lactose | 100 |
| Magnesium stearate | 2 |

The above components were mixed with each other and then filled into a gelatin capsule according to a conventional method, thereby preparing a capsule formulation containing *Cirsium japonicum* extract as an active ingredient.

INDUSTRIAL APPLICABILITY

The composition for stimulating melanogenesis comprising *Cirsium japonicum* extract as an effective ingredient has no skin irritation and cytotoxicity and is excellent in human stability and very effective in stimulating melanogenesis. Therefore, the composition can be safely used in cosmetic or pharmaceutical composition for preventing, improving or treating vitiligo, white hair or hypopigmentation.

The invention claimed is:

1. A method for stimulating melanogenesis, comprising administering a composition which comprises *Cirsium japonicum* flower extract as an effective ingredient to a patient in need thereof.

2. A method for preventing or reducing vitiligo, white hair or hypopigmentation, comprising administering a composition which comprises *Cirsium japonicum* flower extract as an effective ingredient to a patient in need thereof.

3. The method according to claim 2, wherein the flower *Cirsium japonicum* extract is comprised in an amount of 0.0001 to 15% by weight, based on the total weight of the composition.

4. The method according to claim 2, wherein the composition has a formulation selected form the group consisting of a solution, a suspension, an emulsion, a paste, a gel, a cream, a lotion, a powder, a soap, a surfactant-containing cleanser, an oil, a powder foundation, an emulsion foundation, a wax foundation, and a spray.

5. A method for preventing or treating vitiligo, white hair or hypopigmentation, comprising administering a composition which comprises *Cirsium japonicum* flower extract as an effective ingredient to a patient in need thereof.

6. The method according to claim 5, wherein the *Cirsium japonicum* flower extract is comprised in an amount of 0.0001 to 15% by weight, based on the total weight of the composition.

* * * * *